US008940789B2

(12) United States Patent
Kusano et al.

(10) Patent No.: US 8,940,789 B2
(45) Date of Patent: Jan. 27, 2015

(54) NEURITE ELONGATION AGENT, MEMORY-IMPROVING AGENT AND ANTI-ALZHEIMER AGENT COMPRISING 4'-DEMETHYLNOBILETIN OR 4'-DEMETHYLTANGERETIN AS ACTIVE INGREDIENT, AND PROCESS FOR PRODUCTION OF THE COMPOUND

(75) Inventors: Shuichi Kusano, Sakaide (JP); Hiroshi Tamura, Marugame (JP)

(73) Assignee: Fuji Sangyo Co., Ltd., Marugame-shi, Kagawa (JP)

( * ) Notice: Subject to any disclaimer, the term of this patent is extended or adjusted under 35 U.S.C. 154(b) by 0 days.

(21) Appl. No.: 13/321,988

(22) PCT Filed: Mar. 10, 2010

(86) PCT No.: PCT/JP2010/053958
§ 371 (c)(1),
(2), (4) Date: Nov. 22, 2011

(87) PCT Pub. No.: WO2010/140409
PCT Pub. Date: Dec. 9, 2010

(65) Prior Publication Data
US 2012/0101152 A1   Apr. 26, 2012

(30) Foreign Application Priority Data

Jun. 3, 2009   (JP) ................... 2009-133598

(51) Int. Cl.
| | | |
|---|---|---|
| *A61K 31/352* | (2006.01) | |
| *A61P 25/00* | (2006.01) | |
| *A61P 25/28* | (2006.01) | |
| *C12P 17/06* | (2006.01) | |
| *C07D 311/30* | (2006.01) | |
| *A61K 36/062* | (2006.01) | |
| *A61K 36/752* | (2006.01) | |

(52) U.S. Cl.
CPC ............... *C12P 17/06* (2013.01); *A61K 31/352* (2013.01); *A61K 36/062* (2013.01); *A61K 36/752* (2013.01); *C07D 311/30* (2013.01)
USPC ............................. 514/456; 435/125; 549/403

(58) Field of Classification Search
USPC ............................. 514/456; 435/125; 549/403
See application file for complete search history.

(56) References Cited

U.S. PATENT DOCUMENTS

2002/0040052 A1   4/2002   Ito et al.

FOREIGN PATENT DOCUMENTS

JP   2003-102430 A   4/2003

OTHER PUBLICATIONS

Didier Buisson et al., "Biotransformation of Polymethoxylated Flavonoids: Access to Their 4'-O-Demethylated Metabolites," *J. Nat. Prod.*, (2007), vol. 70, No. 6, pp. 1035-1038.
Shiming Li et al., "Anti-Inflammatory Property of the Urinary Metabolites of Nobiletin in Mouse," *Bioorganic & Med. Chem. Letters*, (2007), vol. 17, No. 18, pp. 5177-5181.
Michael Fernández et al., "Quantitative Structure-Activity Relationship to Predict Differential Inhibition of Aldose Reductase by Flavonoid Compounds," *Bioorganic & Med. Chem.*, (2005), vol. 13, No. 9, pp. 3269-3277.
Hiroshi Onozuka et al., "Nobiletin, a Citrus Flavonoid, Improves Memory Impairment and Aβ Pathology in a Transgenic Mouse Model of Alzheimer's Disease " *The Journal of Pharmacology and Experimental Therapeutics*, vol. 326, No. 3, (2008), pp. 739-744.
Nobuyuki Koga et al., "Comparative Study on Nobiletin Metabolism with Liver Microsomes from Rats, Guinea Pigs and Hamsters and Rat Cytochrome P450," *Biol. Pharm. Bull.*, vol. 30, No. 12, (2007), pp. 2317-2323.
English-language International Search Report for PCT/JP2010/053958.
Gu et al., "Recombinant human NGF-loaded microspheres promote survival of basal forebrain cholinergic neurons and improve memory impairments of spatial learning in the rat model of Alzheimer's disease with fimbria-fornix lesion," *Neuroscience Letters*, 453 (2009), 204-209.

*Primary Examiner* — San-Ming Hui
*Assistant Examiner* — Kathrien Cruz
(74) *Attorney, Agent, or Firm* — Holtz, Holtz, Goodman & Chick PC

(57) ABSTRACT

A method for producing 4'-demethylnobiletin or 4'-demethyltangeretin including fermenting a skin derived from at least one citrus fruit selected from citrus fruits belonging to section *Acrumen* in subgenus *Metacitrus* in genus *Citrus* or citrus fruits belonging to section *Aurantium* in subgenus *Archicitrus* in genus *Citrus*, or a water extract product thereof using one or more *Aspergillus* molds selected from *Aspergillus kawachii*, *Aspergillus awamori*, *Aspergillus oryzae*, *Aspergillus sojae*, *Aspergillus saitoi*, and *Aspergillus usamii* to obtain a fermented product.

1 Claim, 4 Drawing Sheets

4'-DEMETHYLNOBILETIN
(PRODUCT OF EXAMPLE 3)

4'-DEMETHYLTANGERETIN
(PRODUCT OF EXAMPLE 3)

NOBILETIN
(COMPARATIVE CONTROL)

TANGERETIN
(COMPARATIVE CONTROL)

ONLY ETHANOL
(CONTROL)

NEURITE ELONGATION AGENT, MEMORY-IMPROVING AGENT AND ANTI-ALZHEIMER AGENT COMPRISING 4'-DEMETHYLNOBILETIN OR 4'-DEMETHYLTANGERETIN AS ACTIVE INGREDIENT, AND PROCESS FOR PRODUCTION OF THE COMPOUND

CROSS-REFERENCE TO RELATED APPLICATION

This application is a United States national phase application of International Application PCT/JP2010/053958 filed Mar. 10, 2010.

TECHNICAL FIELD

The present invention relates to a production method for 4'-demethylnobiletin or 4'-demethyltangeretin, comprising fermenting a skin of a specific species of citrus fruit using a specific species of *Aspergillus* mold to obtain a fermented product. The present invention also relates to a pharmaceutical preparation (a neurite elongation agent, a memory-improving agent, or an anti-Alzheimer's agent) containing the compound as an active ingredient.

BACKGROUND ART

Nobiletin and tangeretin, which are polymethoxyflavonoids, are citrus fruit-specific flavonoids, and in recent years, the compounds have been found to have a variety of physiological activities such as cancer-preventive, senescence-retarding, and anti-atherogenic activities. In addition, it has been reported that nobiletin has an Alzheimer's-improving activity (see Non Patent Literature 1) and a neurite elongation activity (see Patent Literature 1).

On the other hand, all the studies on the physiological activities of nobiletin and tangeretin have been made for nobiletin and tangeretin per se (unchanged compounds), but recent reports show that the compounds are absorbed from the intestinal mucosa and metabolized into some demethylated compounds, and 6 methoxy groups in all are partially demethylated (see Non Patent Literature 2).

An example of a study on a cancer-suppressing activity of nobiletin using the following synthesized demethylated compounds shows that with respect to the effect of preventing development of cancer by suppressing synthesis of nitric oxide (NO), inducible nitric oxide synthase (iNOS), and cyclooxygenase-2 (COX-2), wherein NO, iNOS and COX-2 promote inflammation and development of cancer, three kinds of demethylated demethylnobiletins (in particular, 3'-demethylnobiletin, 4'-demethylnobiletin, and 3',4'-didemethylnobiletin) each have a drastically higher effect than nobiletin per se. In particular, 4'-demethylnobiletin has a high activity (see Non Patent Literature 3).

A study on the physiological activities of two kinds of polymethoxyflavonoids (in particular, 5-hydroxy-3,6,7,8,3', 4'-hexamethoxyflavone and 3'-hydroxy-5,6,7-trimethoxyflavone) having a hydroxyl group at position 5 or 3' and obtained from an orange as polymethoxyflavonoids which are present in a citrus fruit and have a hydroxyl group also show that the compounds suppress strongly expression of mRNA of iNOS and COX-2 and induce apoptosis of breast cancer cells.

Both the studies suggest that the physiological functions of polymethoxyflavonoids are significantly enhanced by substituting part of the methoxy groups with hydroxyl groups, and the demethyl polymethoxyflavonoids are expected to be used as functional components.

However, the contents of such polymethoxyflavonoids which are contained in any currently known natural substance and in which part of methoxy groups have been substituted by hydroxyl groups are very low, and hence it is not realistic to extract and use the component using these substances as raw materials.

CITATION LIST

Patent Literature

[Patent Literature 1] JP 2002-60340 A

Non Patent Literature

[Non Patent Literature 1] J Pharmacol Exp Ther. 2008, 326: 739

[Non Patent Literature 2] Koga N. et al.: Biol. Pharm. Bull., 2007, 30:2317

[Non Patent Literature 3] Li S. et al.: Bioorg. Med. Chem. Lett., 2007, 17:5177

SUMMARY OF INVENTION

Technical Problem

An object of the present invention is to solve the above-mentioned problems and to produce a demethyl polymethoxyflavonoid having an excellent physiological activity by a method for which a raw material is readily available and which includes a simple step and is highly safe for oral ingestion.

Solution to Problem

In view of such circumstances, the inventors of the present invention have attempted a variety of bioconversions using the skin of a citrus fruit containing polymethoxyflavonoids at a high content and as a result have found that partially-demethylated polymethoxyflavonoids are generated by fermentation by a specific species of *Aspergillus* mold. Then, the inventors have clarified that the compounds have molecular structures of 4'-demethylnobiletin and 4'-demethyltangeretin, each of which has an excellent cancer-preventive activity and is substituted by a hydroxyl group at position 4'.

Meanwhile, the inventors of the present invention have found for the first time that each of 4'-demethylnobiletin and 4'-demethyltangeretin has a neurite elongation activity. Further, the inventors have found that the compounds have obviously enhanced activities compared with unchanged compounds, i.e., nobiletin and tangeretin. In addition, the inventors have also found that the compounds have excellent memory-improving activities.

The present invention has been made based on such findings.

That is, a first aspect of the present invention relates to a production method for 4'-demethylnobiletin, comprising fermenting a skin of citrus fruits or its water extract product using one or more *Aspergillus* molds selected from *Aspergillus kawachii, Aspergillus awamori, Aspergillus oryzae, Aspergillus sojae, Aspergillus saitoi*, and *Aspergillus usamii* to obtain a fermented product, wherein the skin is derived from at least one citrus fruit selected from citrus fruits belonging to section *Acrumen* in subgenus *Metacitrus* in genus

*Citrus* or citrus fruits belonging to section *Aurantium* in subgenus *Archicitrus* in genus *Citrus*.

Further, a second aspect of the present invention relates to a production method for 4'-demethyltangeretin, comprising fermenting a skin of citrus fruits or its water extract product using one or more *Aspergillus* molds selected from *Aspergillus kawachii*, *Aspergillus awamori*, *Aspergillus oryzae*, *Aspergillus sojae*, *Aspergillus saitoi*, and *Aspergillus usamii* to obtain a fermented product, wherein the skin is derived from at least one citrus fruit selected from citrus fruits belonging to section *Acrumen* in subgenus *Metacitrus* in genus *Citrus* or citrus fruits belonging to section *Aurantium* in subgenus *Archicitrus* in genus *Citrus*.

Further, a third aspect of the present invention relates to a neurite elongation agent, which contains 4'-demethylnobiletin as an active ingredient.

Further, a fourth aspect of the present invention relates to a neurite elongation agent, which contains 4'-demethyltangeretin as an active ingredient.

Further, a fifth aspect of the present invention relates to a neurite elongation agent, which contains 4'-demethylnobiletin and 4'-demethyltangeretin as active ingredients.

Further, a sixth aspect of the present invention relates to a memory-improving agent or anti-Alzheimer's agent, which contains 4'-demethylnobiletin as an active ingredient.

Further, a seventh aspect of the present invention relates to a memory-improving agent or anti-Alzheimer's agent, which contains 4'-demethyltangeretin as an active ingredient.

Further, an eight aspect of the present invention relates to a memory-improving agent or anti-Alzheimer's agent, which contains 4'-demethylnobiletin and 4'-demethyltangeretin as active ingredients.

Advantageous Effects of Invention

The present invention enables easy and large-scale production of 4'-demethylnobiletin and 4'-demethyltangeretin, which are excellent functional components, by fermentation of a specific citrus fruit used as a raw material using a specific *Aspergillus* mold (by a method for which a raw material is very readily available and which includes a very simple step).

The present invention also enables the provision of 4'-demethylnobiletin and 4'-demethyltangeretin, which are derived from a natural edible plant and are safe.

The present invention also enables the provision of a functional food or beverage or a pharmaceutical preparation (a cancer-preventive agent, a neurite elongation agent, a memory-improving agent, or an anti-Alzheimer's agent) containing 4'-demethylnobiletin or 4'-demethyltangeretin described above as an active ingredient.

DESCRIPTION OF EMBODIMENTS

Figure 1:
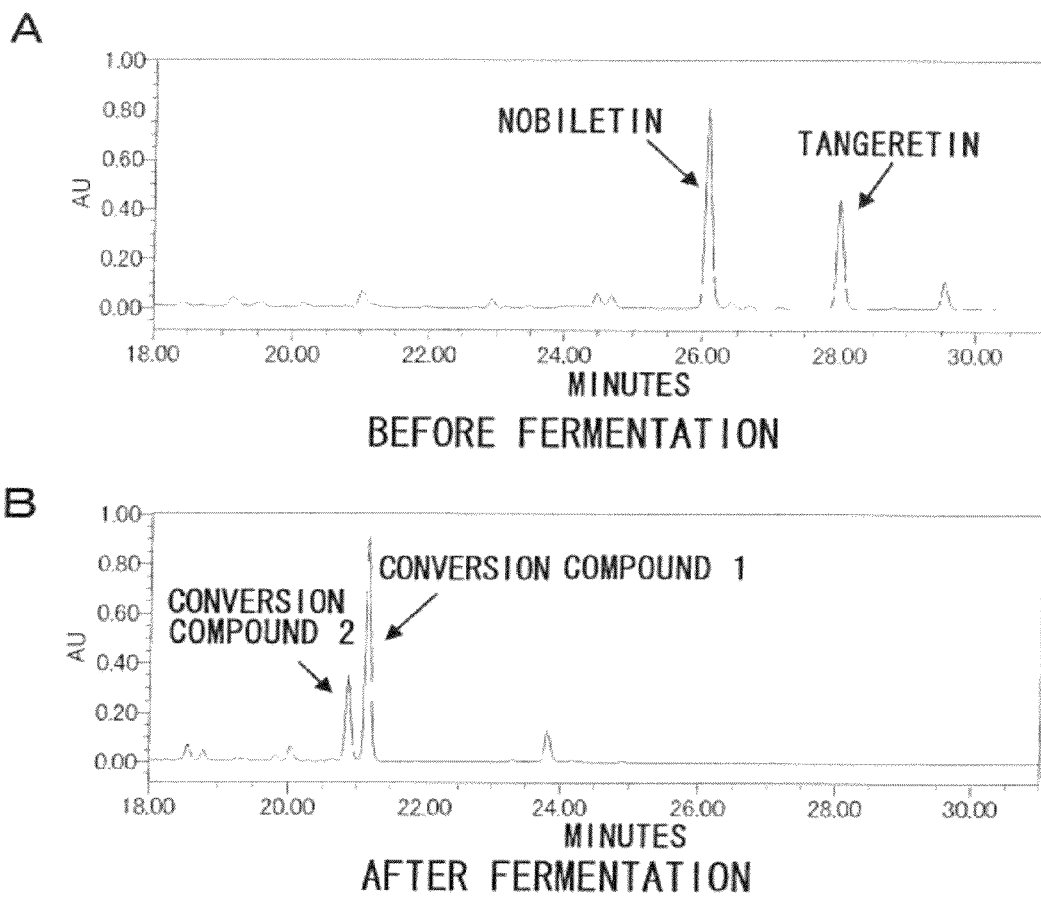
FIG. 1 are diagrams showing the results of HPLC analyses before and after fermentation by an *Aspergillus* mold in Example 1.

Hereinafter, the present invention is described in detail.

The present invention relates to a production method for 4'-demethylnobiletin or 4'-demethyltangeretin, comprising fermenting a skin of a specific species of citrus fruit using a specific species of *Aspergillus* mold to obtain a fermented product. The present invention also relates to a pharmaceutical preparation (a neurite elongation agent, a memory-improving agent, or an anti-Alzheimer's agent) containing the compound as an active ingredient.

[Raw Material]

A raw material which may be used in the present invention is a 'skin' of a citrus fruit which contains polymethoxyflavonoids (specifically, nobiletin and tangeretin). It should be noted that a fruit (the whole fruit including skin, juice, pulp, and seed) may be used, but use of the skin alone is desirable from the viewpoint of the polymethoxyflavonoid content and efficient use of wastes.

It should be noted that a raw material containing other parts (such as leaf, germ, stem, and flower) of the citrus fruit plant may be used, but the material desirably does not contain these parts from the viewpoint of the polymethoxyflavonoid content.

Any citrus fruit belonging to the section *Acrumen* in subgenus *Metacitrus* or section *Aurantium* in subgenus *Archicitrus* both in genus *Citrus* may be used regardless of the breed and strain.

Here, the section *Acrumen* in subgenus *Metacitrus* or the section *Aurantium* in subgenus *Archicitrus* are taxonomic groups defined by Tyozaburo Tanaka's classification (Tanaka T., Bull. Univ. Osaka Pref., Ser. B. 21, 139-145 (1969)), and the section *Acrumen* includes *Citrus unshiu*, *Citrus reticulata* (another name: Ponkan), *Citrus mandarin* (another name: Mediterranean mandarin), *Citrus tangerine* (another name: Dancy tangerine), *Citrus succosa*, *Citrus tachibana*, *Citrus kinokuni*, *Citrus depressa*, *Shikaikan*, *Citrus erythrosa*, and *Citrus keraji*.

Meanwhile, the section *Aurantium* includes Sweet orange, *Citrus sinensis* Valencia, *Citrus iyo*, *Citrus tamurana*, and *Citrus shunkokan*.

In particular, *Citrus reticulata* (another name: Ponkan), *Citrus depressa*, *Citrus tangerine*, and *Citrus tachibana* of the section *Acrumen* are preferred from the viewpoint of the polymethoxyflavonoid content and effective use of wastes.

The citrus fruit used in the present invention as the raw material is preferably a raw fruit harvested and collected or a fruit washed with water, but a dried, frozen, or long-term preserved fruit may be used.

Further, in the present invention, the citrus fruit used as the raw material may be used as it is, but is preferably subjected to a treatment by any one of cutting, fragmentating, and grinding.

This step includes a variety of treatments for the citrus fruit used as the raw material, such as cutting into some large pieces, cutting into small pieces, crushing, grinding, and pulverizing. This step is preferably carried out by cutting the raw material into large pieces with sizes of about one to a few centimeters.

Further, an extract product (extract or dried product) obtained by extracting the polymethoxyflavonoids in advance (in particular, water extraction) from such raw material or products isolated as pure polymethoxyflavonoids may be used.

It should be noted that, with regard to conditions for the water extract product, the extraction may be carried out by adding the solvent in an amount 1 to 50 times (weight ratio), preferably 2 to 15 times that of the fruit skin and subjecting the mixture to immersion or shaking for 5 minutes to one month, preferably 20 minutes to one week under a temperature condition ranging from 0° C. to the boiling point of the solvent, preferably from room temperature to a temperature equal to or lower than the boiling point of the solvent.

Further, in particular, water extraction at high temperature (hot-water extraction) is desirably performed. Specifically, extraction is desirably performed at 90° C. or more (preferably in a boiling state) for about several minutes to several hours (for example, 5 minutes to 5 hours).

The extract liquid (extract) obtained after extraction may be used as it is in the following fermentation by an *Aspergillus* mold, but is desirably filtrated or centrifuged to remove solid matter (residues of the fruit skin or the like).

It should be noted that the extraction efficiency can be improved by performing the extraction for a plurality of times by adding a solvent again to the removed solid matter.

The thus obtained extract liquid (extract) may be subjected to a drying treatment (freeze-dried, dried using an evaporator, or the like) to prepare a dried product.

[Fermentation by *Aspergillus* Mold]

The present invention includes a step of performing fermentation by an *Aspergillus* mold using a fermentation raw material prepared as described above (a fruit skin, or a water extract product of the skin) as substrate to obtain a fermented product.

It should be noted that the above-mentioned fermentation raw material is preferably subjected to a heat treatment before the fermentation by the *Aspergillus* mold to sterilize unwanted bacteria in the raw material.

As the *Aspergillus* mold for fermenting the raw material, there may be used *Aspergillus kawachii, Aspergillus awamori, Aspergillus oryzae, Aspergillus sojae, Aspergillus saitoi,* or *Aspergillus usamii*. Further, these *Aspergillus* molds may be used in combination.

Of the *Aspergillus* molds, *Aspergillus kawachii, Aspergillus awamori,* and *Aspergillus oryzae* are preferably used because 4'-demethylnobiletin and 4'-demethyltangeretin may each be obtained at a high content.

In a method of inoculating the above-mentioned *Aspergillus* mold into the raw material for fermentation, spores of the *Aspergillus* mold may be directly sprinkled on the raw material for fermentation to allow the spores to adhere thereto. Alternatively, the above-mentioned *Aspergillus* mold may be inoculated by spreading a medium obtained in advance by prefermentation of the *Aspergillus* mold by liquid culture throughout the fermentation raw material.

In the case where the above-mentioned *Aspergillus* mold is inoculated into the raw material for fermentation, fermentation of the microorganism is desirably performed under aerobic conditions, and hence for example, a cylindrical shallow container having a wide bottom is preferably used.

The raw material for fermentation may be spread uniformly on the bottom of such container to increase a contact area with air.

Meanwhile, in the case where the raw material for fermentation is a liquid, a treatment such as aeration or stirring is desirably performed.

The fermentation is performed under conditions suitable for growth of the above-mentioned *Aspergillus* mold, i.e., at a temperature of preferably 10 to 40° C., more preferably 20 to 40° C., still more preferably 25 to 32° C. In addition, the fermentation is preferably performed under conditions suitable for growth of the above-mentioned *Aspergillus* mold, i.e., in the dark. Moreover, in the case where the fermentation raw material is not a liquid, the raw material preferably contains water sufficiently (for example, a water content of 25% or more).

The fermentation period of microorganism fermentation for producing large amounts of 4'-demethylnobiletin and 4'-demethyltangeretin is preferably 2 to 21 days, more preferably 3 to 14 days, still more preferably 4 to 12 days.

In the case where the fermentation period is less than 2 days, 4'-demethylnobiletin and 4'-demethyltangeretin cannot be obtained sufficiently because microorganism fermentation by the above-mentioned *Aspergillus* mold is hardly progressed. In contrast, in the case where the period exceeds 21 days, 4'-demethylnobiletin and 4'-demethyltangeretin generated by microbial conversion are progressively decomposed resulting in eliminating good fragrance derived from the citrus fruit.

Meanwhile, in the fermentation by the *Aspergillus* mold in the present invention, a polymethoxyflavonoid is demethylated with an enzyme secreted from the *Aspergillus* mold into a demethyl polymethoxyflavonoid.

Therefore, instead of the fermentation by the *Aspergillus* mold, solution extraction from the *Aspergillus* mold or a fermented product obtained after the fermentation may be performed to prepare an enzyme solution containing an enzyme capable of demethylating the polymethoxyflavonoid, followed by an enzymatic reaction with the raw material using the enzyme to prepare a reaction product, to thereby obtain the demethyl polymethoxyflavonoid.

Specifically, the enzymatic reaction can be performed by collecting a water solution from the fermented product after the fermentation by the *Aspergillus* mold and using the water solution as a crude enzyme solution.

When fermentation by the *Aspergillus* mold of the present invention is performed, all of nobiletin and tangeretin, which are polymethoxyflavonoids in the citrus fruit raw material, are converted into 4'-demethylnobiletin and 4'-demethyltangeretin.

Specifically, fermentation of the citrus fruit raw material by the *Aspergillus* mold can produce an *Aspergillus* mold-fermented product containing 4'-demethylnobiletin and 4'-demethyltangeretin at high contents, i.e., containing 4'-demethylnobiletin at a content of about 0.5 to 1.5% by mass based on dry weight (specifically, about 1% by mass) and 4'-demethyltangeretin at a content of 0.25 to 0.75% by mass based on dry weight (specifically, about 0.5% by mass).

Therefore, the *Aspergillus* mold-fermented product obtained as described above may be used as a raw material for drugs or functional foods as it is or after processing (for example, fragmentating, grinding, pulverizing, drying, or the like) the material.

[Solution Extraction]

It should be noted that, in view of the purity, the extract product is desirably obtained by solution extraction from the fermented product obtained after the fermentation by the *Aspergillus* mold.

The solution extraction step may be carried out directly for the *Aspergillus* mold-fermented product, but is more desirably carried out for a product obtained by treating the *Aspergillus* mold-fermented product by any one of fragmentating, crushing, grinding, pulverizing, and the like.

The solvent to be used in the solution extraction step may be water, a buffer, an organic solvent, or a water-containing solvent thereof. Examples of the organic solvent include: a lower aliphatic alcohol such as ethanol, methanol, isopropanol, or butanol; acetone; ethyl acetate; and chloroform.

Of those solvents, water, ethanol, or water-containing ethanol is particularly preferred from the viewpoints of extraction efficiency, handling, and safety.

Further, the extraction is particularly preferably carried out using ethanol having a final concentration of 55% or more, preferably 60% or more, more preferably 80% or more because it is possible to suppress elution of impurities, i.e., polysaccharides and to improve the extraction efficiency of the demethyl polymethoxyflavonoid.

With regard to extraction conditions, the extraction may be carried out by adding the solvent in an amount 1 to 50 times (weight ratio), preferably 2 to 15 times that of the raw material (preferably a fragmented product) and subjecting the mixture to immersion or shaking for 5 minutes to one month, preferably 20 minutes to one week under a temperature condition ranging from 0° C. to the boiling point of the solvent, preferably from room temperature to a temperature equal to or lower than the boiling point of the solvent.

The resultant extract liquid may be freeze-dried or dried using an evaporator or the like to prepare a concentrated and dried product.

Further, the solution extraction step may be carried out for a plurality of times using a plurality of different solvents. In particular, in the case where the first extraction is carried out using water or a low concentration of a water-containing alcohol, the extraction efficiency of the demethyl polymethoxyflavonoid can be improved by subsequently performing extraction using ethanol having a concentration equal to or higher than the above-mentioned specific concentration.

Then, the extract product obtained as described above (the above-mentioned extract liquid or concentrated and dried product) may be used as a raw material for drugs and functional foods.

[Purification]

Further, the extract or product may be subjected to a purification step to improve the purity.

The purification step can improve the purity by liquid-liquid separation extraction or by column purification using, for example, silica gel, chemically modified silica gel, activated carbon, or a synthetic adsorption resin carrier.

As an example, purification conditions for improving the purity of the demethyl polymethoxyflavonoid are shown.

First, a liquid obtained by removing ethanol from the extract liquid (specifically, an extract liquid obtained through ethanol extraction) is charged to a column including a porous synthetic adsorption resin (specifically, DIAION HP-20 [manufactured by Mitsubishi Chemical Corporation]) equilibrated with water. Then, components eluted with water are removed, and a liquid eluted with 39 to 41% ethanol (specifically, 40% ethanol) is further removed. Next, a component eluted with 44 to 46% ethanol (specifically, 45% ethanol) is collected, to thereby obtain a demethyl polymethoxyflavonoid-containing composition having an improved purity.

It should be noted that, when the extraction and purification are carried out under the preferred conditions described in the foregoing, a demethyl polymethoxyflavonoid-rich composition having a purity of 80% or more can be obtained.

Further, the demethyl polymethoxyflavonoid-containing composition obtained as described above may further be subjected to ODS column chromatography (specifically, eluted with 45% methanol), thin-layer chromatography (TLC) [specifically, hexane/ethanol (7:3)], or ODS-HPLC (specifically, a mixed solvent of 37% (v/v) acetonitrile in water), and target peaks are collected, to thereby isolate a pure product of each demethyl polymethoxyflavonoid.

Specifically, the demethyl polymethoxyflavonoids obtained as described above are "4'-demethylnobiletin" (see the following chemical formula 1) and "4'-demethyltangeretin" (see the following chemical formula 2).

The compounds are monodemethylated products of nobiletin and tangeretin obtained by demethylation at position 4'. The compounds are more highly polar due to the demethylation and are excellent in solubility in alcohols and water compared with the respective unchanged compounds.

[Chem. 1]

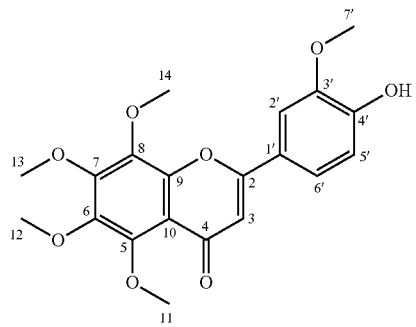

[Chem. 2]

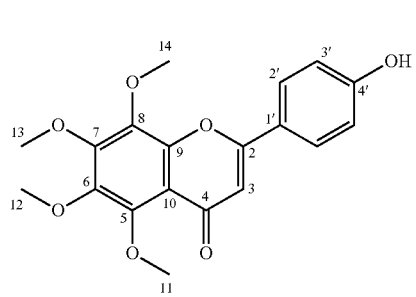

[Physiological Activity]

4'-Demethylnobiletin and 4'-demethyltangeretin obtained as described above have excellent "neurite elongation activities" compared with the unchanged compounds (nobiletin and tangeretin). In addition, the compounds have clinically excellent "memory-improving activities" and "anti-Alzheimer's activities" and provide effective therapeutic, improving, and preventive activities for dementia and Alzheimer's disease. It should be noted that the compounds also have effective improving and preventive activities for amnesia and memory loss of healthy subjects.

Further, the compounds are expected to provide effective therapeutic, improving, and preventive activities for other neurological diseases which may be improved by the neurite elongation activities.

In addition, 4'-demethylnobiletin and 4'-demethyltangeretin have excellent "cancer-preventive activities" compared with the unchanged compounds (nobiletin and tangeretin). In particular, 4'-demethylnobiletin has an extremely high activity (see Li S. et al.: Bioorg. Med. Chem. Lett., 2007, 17:5177).

The "cancer-preventive activities" as used herein specifically include prevention of cancer development by: suppressing synthesis of nitric oxide (NO), inducible nitric oxide synthase (iNOS), and cyclooxygenase-2 (COX-2); or induction of apoptosis in breast cancer cells.

[Drug and Functional Food or Beverage]

4'-Demethylnobiletin or 4'-demethyltangeretin obtained as described above (specifically, as an '*Aspergillus* mold-fermented product,' a 'solution extract product after fermentation,' a 'purified product,' or an 'isolated product') may be used as an active ingredient in a drug or a functional food or beverage by mixing the compound with a variety of raw materials.

It should be noted that the compounds are 'demethyl polymethoxyflavonoids' obtained by demethylation of polymethoxyflavonoids and hence are highly polar and have excellent solubility in water compared with unchanged polymethoxyflavonoids. Therefore, the compounds can be applied to forms to which the polymethoxyflavonoids have had a difficulty in being applied.

In addition, the compounds may be used so that only each of the compounds is contained or both of the compounds are contained.

With regard to an effective dose of 4'-demethylnobiletin or 4'-demethyltangeretin, when the compound is orally ingested in an amount of 1 mg or more, preferably 10 mg or more per adult with a body weight of 60 kg per day, the above-mentioned excellent physiological activities (in particular, neurite elongation activity, memory-improving activity, and anti-Alzheimer's activity) can be obtained.

Therefore, when 4'-demethylnobiletin or 4'-demethyltangeretin is ingested in and by such a form and ingestion method (number of times, dose) that ensure the required amount, the above-mentioned pharmacological activities are expected to be obtained. However, the form and ingestion method are desirably appropriately determined depending on the age, weight, and symptom of a subject, an ingestion schedule, a preparation form, and the like.

Meanwhile, the contents of the compounds in a drug or functional food or beverage may be an amount for securing the above-mentioned necessary ingestion dose, and specifically, the content is 0.1% by mass or more, preferably 0.5% by mass or more, more preferably 3% by mass or more. In addition, the upper limit is, for example, 50% by mass or less.

As the 'drug,' the compound may be formed into, for example, a powder, a particulate, a granule, a capsule in which the compound is filled, a solution where the compound is dispersed in water, or a tablet obtained by blending the compound with a filler and the like.

Further, as the 'functional food or beverage,' the compound may be mixed with various food raw materials and added to, for example, a biscuit, a snack, a chewing gum, a chewable tablet, a refreshing beverage, a drink, a soup, a jelly, or a candy.

It should be noted that 4'-demethylnobiletin and 4'-demethyltangeretin obtained as described above are considered to be effective for all mammals. Therefore, the compounds may be converted into forms suitable for drugs for pets and livestock by conventional means. Further, the compounds may be converted into forms of feeds and pet foods.

EXAMPLES

Hereinafter, the present invention is described by way of examples, but the scope of the present invention is not limited by the examples.

Example 1

Fermentation of Fruit Skin of *Citrus reticulata* (Another Name: Ponkan) by *Aspergillus* Mold (*Aspergillus awamori*)

The fruit skin of *Citrus reticulata* (another name: Ponkan) was used as a raw material for fermentation. 500 g of the fruit skin of *Citrus reticulata* (another name: Ponkan) were fragmentated by cutting and spread uniformly on a wide-bottom container (a cylindrical container having a bottom) sterilized by an autoclave to achieve good airflow, and a small amount of water was added thereto, followed by heating for 30 minutes.

*Aspergillus awamori* (manufactured by Bioc) was inoculated throughout the thus-obtained fruit skin of *Citrus reticulata* (another name: Ponkan). Then, a microorganism fermentation treatment (fermentation by the *Aspergillus* mold) was aerobically performed in the dark in a 30° C. incubator for 10 days, to thereby obtain an *Aspergillus* mold-fermented product.

Then, HPLC analyses were performed for the fermented product. FIG. 1 show the results. It should be noted that, in FIG. 1, FIG. 1A shows the results of the analysis for the fruit skin of *Citrus reticulata* (another name: Ponkan) before fermentation, and FIG. 1B shows the results of the analysis for the fermented product obtained after fermentation by the *Aspergillus* mold.

The results show that nobiletin and tangeretin present before the fermentation completely disappeared, and after fermentation, were converted into polymethoxyflavonoid-conversion compounds (conversion compounds 1 and 2 shown by the peaks in FIG. 1) obtained by some sort of elimination of functional group.

That is, it was found that fermentation of the fruit skin of *Citrus reticulata* (another name: Ponkan) used as a raw material by the *Aspergillus* mold produced a composition containing the polymethoxyflavonoid-conversion compounds shown in FIG. 1.

Example 2

Preparation of Composition Containing Demethyl Polymethoxyflavonoid at High Content The *Aspergillus* mold-fermented product obtained in Example 1 above (1 kg) was fragmented by grinding, and 5 L of ethanol were added, followed by extraction at room temperature for 3 days, to thereby obtain an extract liquid.

Subsequently, the resultant extract liquid was filtrated using filter paper, and the filtrate was concentrated to 1 L using a rotary evaporator. Then, 5 L of water were added, to thereby obtain an aqueous solution.

The resultant solution was charged to DIAION HP20 (a porous synthetic adsorption resin column) preliminarily equilibrated with water, and unadsorbed components were removed by 3 L of water. Then, components eluted with 2 L of 40% ethanol were removed. Subsequently, components eluted with 2 L of 45% ethanol were obtained.

Then, the resultant eluted components were concentrated to dryness using an evaporator, to thereby obtain a composition containing the above-mentioned polymethoxyflavonoid-conversion compounds 1 and 2 at high contents.

Example 3

Isolation and Purification of Demethyl Polymethoxyflavonoid

The composition obtained in Example 2 above (2 g) was dissolved in 20% methanol and subjected to ODS column chromatography (a column with an inner diameter of 20 mm and a length of 30 cm was filled with 30 g of Wakogel 50C18). Components eluted with 40% methanol were removed, and components eluted with 60% methanol were obtained.

Subsequently, the resultant components were subjected to preparative TLC chromatography (silica gel 70PF$_{254}$ Plate Wako, film thickness 0.75 mm, manufactured by Wako Pure Chemical Industries, Ltd.) under conditions of a developing solvent hexane/ethanol 7:3, and fractions containing the respective conversion compounds were collected while confirming the compounds with a UV lamp.

Then, the resultant fractions were each charged to a preparative HPLC column (TSK GEL ODS, manufactured by TOSOH CORPORATION, 4.6 mm×25 cm), and pure polymethoxyflavonoid-conversion compounds 1 and 2 were separately isolated using a mobile phase of 37% (v/v) acetonitrile.

Example 4

Structural Analysis of Conversion Compound 1 (4'-Demethylnobiletin)

The isolated product of the polymethoxyflavonoid-conversion compound 1 obtained in Example 3 above was subjected to FAB mass spectrometry (pos) (JMS-600Y) to measure the molecular weight.

Further, structural analysis was performed by $^1$H-NMR and $^{13}$C-NMR. JNM-AL400 (NMR) (manufactured by JEOL Ltd.) was used as an apparatus for measurement and the measurement was performed by detecting signals at 400 MHz for $^1$H-NMR and at 100 MHz for $^{13}$C-NMR. δH (ppm) and δC (ppm) were measured for $^1$H and $^{13}$C of the substance of interest, respectively.

Table 1 shows the results of a comparison of A-ring carbon signals (ppm) between the polymethoxyflavonoid-conversion compound 1 and tangeretin.

Meanwhile, Table 2 shows the results of measurement of $^1$H and $^{13}$C. Further, Table 2 collectively shows the results of chemical shifts (CDCl$_3$) of the polymethoxyflavonoid-conversion compound 1. It should be noted that, in Table 2, symbols on the right side of numerical values of δH (ppm) represent signal splitting patterns: "s" represents a singlet; "d" represent a doublet; "dd" represents a doublet of doublets; and "m" represents a multiplet.

TABLE 1

| | Comparison of A-ring carbon signals (ppm) | |
|---|---|---|
| Carbon position | Tangeretin (control) | Polymethoxyflavonoid-modified compound 1 |
| 5 | 144.0 | 144.2 |
| 6 | 138.1 | 138.1 |
| 7 | 151.3 | 151.5 |
| 8 | 148.4 | 148.5 |
| 9 | 147.7 | 147.7 |
| 10 | 114.8 | 114.9 |
| OMe | 62.3 | 62.3 |
| | 62.1 | 62.0 |
| | 61.9 | 61.8 |
| | 61.7 | 61.7 |

TABLE 2

| Carbon No. | δC (ppm) | δH (ppm) |
|---|---|---|
| 1 | | |
| 2 | 161.2 | |
| 3 | 106.7 | 6.60 s |
| 4 | 177.4 | |
| 5 | 144.2 | |
| 6 | 138.1 | |
| 7 | 151.5 | |
| 8 | 148.5 | |
| 9 | 147.7 | |
| 10 | 114.9 | |
| 11 | 62.0 | $^a$3.95 s |
| 12 | $^b$61.8 | 4.02 s |
| 13 | $^b$61.7 | 4.10 s |
| 14 | 62.3 | $^a$3.96 s |
| 1' | 123.6 | |
| 2' | 108.3 | 7.40 d |
| 3' | 147.0 | |
| 4' | 149.0 | |
| 5' | 115.1 | 7.04 d |
| 6' | 120.3 | 7.53 dd |
| 7' | 56.1 | 3.99 s |

$^{a,b}$Signals are interchangeable.

The results of the mass spectrometry showed a measured molecular weight [M-H]$^+$ of m/z=389, and hence the molecular weight was considered to be 388.

Further, a comparison between $^1$H-NMR (in deuterochloroform-deuteromethanol) of nobiletin and $^1$H-NMR of the conversion compound 1 showed that six singlet signals probably attributed to methoxy were observed in nobiletin, while five singlet signals probably attributed to methoxy were observed in the demethylnobiletin. The results show that the conversion compound 1 is probably 'demethylnobiletin' obtained by demethylation of one part in the nobiletin structure and is estimated to have a molecular formula of $C_{20}H_{20}O_8$.

Next, attribution of characteristic methoxy protons was performed by $^1$H-NMR, $^{13}$C-NMR, and HMQC spectra, and HMBC analyses were performed based on the results, to thereby identify carbon atoms corresponding to the base of the methoxy.

Of those, as shown in Table 1, C-5, C-6, C-7, and C-8 highly corresponded to signals of carbon atoms constructing the A ring of tangeretin and signals of the methoxy group also corresponded to tangeretin.

As a result, it is estimated that the A ring of the demethylnobiletin has a common structure with nobiletin and tangeretin. Further, the results suggest that the demethylnobiletin was demethylated in the B ring.

In addition, COSY spectra showed that the proton at 7.53 ppm was coupled (J=8.29 Hz) with the adjacent proton at 7.04 ppm and distant-coupled (J=2.20 Hz) with the proton at 7.40 ppm.

An HMBC spectrum analysis for the protons showed that the protons at 7.40 ppm and 7.53 ppm had a signal at C-2 (161.2 ppm), and hence the positions of the protons were determined to be position 2' and position 6', respectively.

Further, HMBC of 2'-H and 5'-H to both the respective carbon atoms at 147.0 ppm and 149.0 ppm constructing the B ring was observed, but HMBC of 6'-H was observed only at 149.0 ppm.

From the results, the respective carbon atoms at 147.0 ppm and 149.0 ppm were attributed to C-3' and C-4', respectively. Here, C-3' (147.0 ppm) is a carbon atom where HMBC is observed from the methoxy protons (3.99 s), and hence the remaining position 4' was determined to be the demethyl site.

Figure 2:
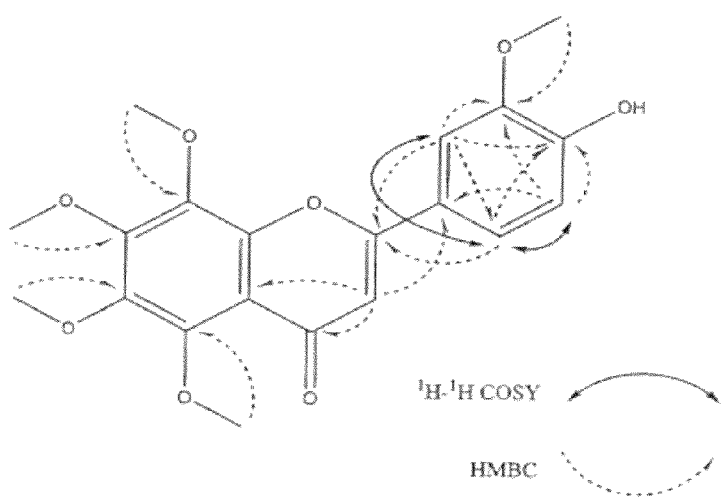
FIG. 2 is a view showing the molecular structure of 4'-demethylnobiletin determined in Example 4.

The above-mentioned results show that the conversion compound 1 isolated in Example 3 is "4'-demethylnobiletin." In addition, the results of $^1$H and $^{13}$C are collectively shown in Table 2. Further, the molecular structure formula and $^1$H-$^1$HCOSY and HMBC signals determined from the overall results of the analyses described above are collectively shown in FIG. 2.

Example 5

Structural Analysis of Conversion Compound 2 (4'-Demethyltangeretin)

The isolated product of the polymethoxyflavonoid-conversion compound 2 obtained in Example 3 above was subjected to FAB mass spectrometry (pos) (JMS-600Y) to measure the molecular weight.

Further, structural analysis was performed by $^1$H-NMR and $^{13}$C-NMR. JNM-AL400 (NMR) (manufactured by JEOL Ltd.) was used as an apparatus for measurement and the measurement was performed by detecting signals at 400 MHz for $^1$H-NMR and at 100 MHz for $^{13}$C-NMR. δH (ppm) and δC (ppm) were measured for $^1$H and $^{13}$C of the substance of interest, respectively.

Table 3 shows the results of a comparison of A-ring carbon signals (ppm) between the polymethoxyflavonoid-conversion compound 2 and tangeretin.

Meanwhile, Table 4 shows the results of measurement of $^1$H and $^{13}$C. Further, Table 4 collectively shows the results of chemical shifts (CDCl$_3$) of the polymethoxyflavonoid-conversion compound 2. It should be noted that, in Table 4, symbols on the right side of numerical values of δH (ppm) represent signal splitting patterns: "s" represents a singlet; "d" represent a doublet; "dd" represents a doublet of doublets; and "m" represents a multiplet.

TABLE 3

| | Comparison of A-ring carbon signals (ppm) | |
|---|---|---|
| Carbon position | Tangeretin (control) | Polymethoxyflavonoid-conversion compound 2 |
| 5 | 144.0 | 144.2 |
| 6 | 138.1 | 138.1 |
| 7 | 151.3 | 151.7 |
| 8 | 148.4 | 148.4 |
| 9 | 147.7 | 147.8 |
| 10 | 114.8 | 114.6 |
| OMe | 62.3 | 62.3 |
| | 62.1 | 62.1 |
| | 61.9 | 61.8 |
| | 61.7 | 61.7 |

TABLE 4

| Carbon No. | δC (ppm) | δH (ppm) |
|---|---|---|
| 1 | | |
| 2 | 161.2 | |
| 3 | 106.1 | 6.60 s |
| 4 | 178.1 | |
| 5 | 144.2 | |
| 6 | 138.1 | |
| 7 | 151.7 | |
| 8 | 148.4 | |
| 9 | 147.8 | |
| 10 | 114.6 | |
| 11 | $^a$62.1 | 3.95 s |
| 12 | $^b$61.8 | 4.02 s |
| 13 | $^b$61.7 | 4.11 s |
| 14 | $^a$62.3 | 3.97 s |
| 1' | 123.0 | |
| 2' | 128.1 | 7.80 d |
| 3' | 116.4 | 7.04 d |
| 4' | 160.1 | |

$^{a,b}$Signals are interchangeable.

The results of the mass spectrometry showed that a measured molecular weight [M-H]$^+$ of m/z=359, and hence the molecular weight was considered to be 358.

Further, a comparison between $^1$H-NMR (in deutero DMSO) of tangeretin and $^1$H-NMR of the conversion compound 2 showed that five singlet signals probably attributed to methoxy were observed in tangeretin, while four singlet signals probably attributed to methoxy were observed in the demethyltangeretin. The results show that the conversion compound 2 is probably 'demethyltangeretin' obtained by demethylation of one part in the tangeretin structure and is estimated to have a molecular formula of C$_{19}$H$_{18}$O$_7$.

Next, attribution of characteristic methoxy protons in the demethyltangeretin was performed by $^1$H-NMR, $^{13}$C-NMR, and HMQC spectra, and HMBC analyses were performed based on the results, to thereby identify carbon atoms corresponding to the base of the methoxy.

Of those, as shown in Table 3, C-5, C-6, C-7, and C-8 highly corresponded to signals of carbon atoms constructing the A ring of tangeretin and signals of the methoxy group also corresponded to tangeretin.

As a result, it was estimated that the A ring of the demethyltangeretin has a common structure with nobiletin and tangeretin. Further, the results suggest that the demethyltangeretin was demethylated in the B ring.

Further, in an analysis for the proton (3-H) at 6.60 ppm, HMBC was observed at 123.0 ppm in addition to 162.1 ppm (C-2), 178.1 ppm (C-4), and 114.6 ppm (C-10) constructing the C ring. The results show that the carbon atom at 123.0 ppm is the carbon at position 1' in the B ring.

Moreover, $^{13}$C-NMR showed that the carbon atoms at 116.4 ppm and 128.1 ppm each had a signal intensity corresponding to two carbon atoms and suggested the presence of a phenol group. From the HMQC spectra, the signals of hydrogen atoms bonded to the carbon atoms at 116.4 ppm and 128.1 ppm were attributed to 7.04 ppm and 7.80 ppm, respectively, and a mutual coupling (J=8.78 Hz) was confirmed between the hydrogen signals.

Here, in an HMBC spectrum analysis for the proton at 7.80 ppm, a signal corresponding to C-2 (161.1 ppm) was confirmed, and the position was attributed to 2'-H, while the adjacent proton at 7.80 ppm was attributed to 3'-H. As a result, the carbon atom at 160.1 ppm where HMBC was observed was attributed to position 4' from both 2'-H and 3'-H, and the site was determined to be the demethyl site.

Figure 3:
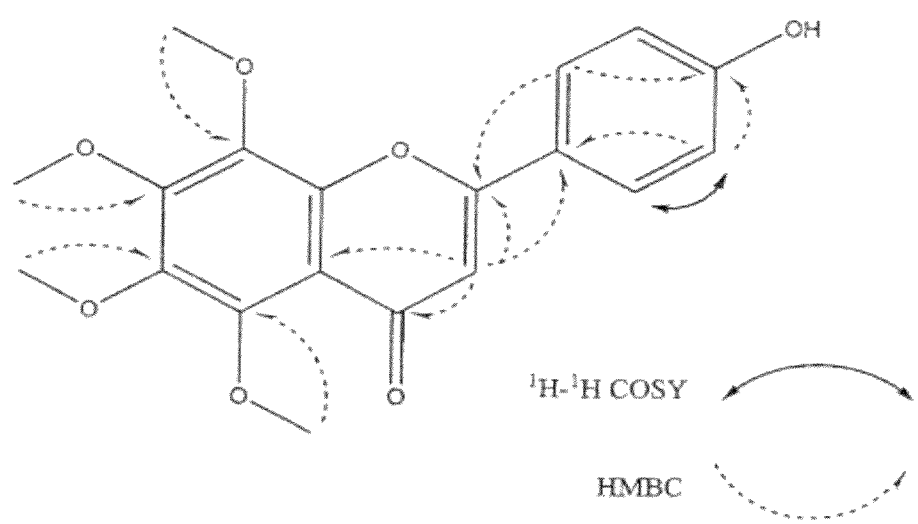
FIG. 3 is a view showing the molecular structure of 4'-demethyltangeretin determined in Example 5.

The above-mentioned results show that the conversion compound 2 isolated in Example 3 is "4'-demethyltangeretin." In addition, the results of $^1$H and $^{13}$C are collectively shown in Table 4. Further, the molecular structure formula and $^1$H-$^1$HCOSY and HMBC signals determined from the overall results of the analyses described above are collectively shown in FIG. 3.

Example 6

Study on Neurite Elongation Activity

The conversion compound 1, i.e., an isolated product of 4'-demethylnobiletin, and the conversion compound 2, i.e., an isolated product of 4'-demethyltangeretin, both obtained in Example 3 above were used to study neurite elongation activities. Neuro2a was used as a neurocyte.

First, Neuro2a cells were cultured in DMEM medium containing 10% fetal bovine serum (FBS) in a 37° C. incubator with 5% CO$_2$. The cells were subcultured every three days.

Then, the cells were inoculated in a 24'-well cell culture plate at 2×10$^4$/well using DMEM medium containing 5% FBS. Three hours after subculture, various test samples were added each at a concentration of 20 μM. 4'-demethylnobiletin (the product in Example 3), 4'-demethyltangeretin (the product in Example 3), nobiletin (a comparative control), and tangeretin (a comparative control) dissolved in ethanol were used as the test samples. As a control, only ethanol was used.

Figure 4:
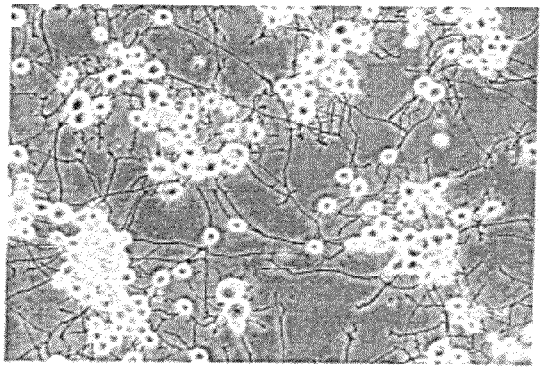
FIG. 4 are picture images for comparing neurite elongation activities of a variety of test samples in Example 6.
Figure 4:
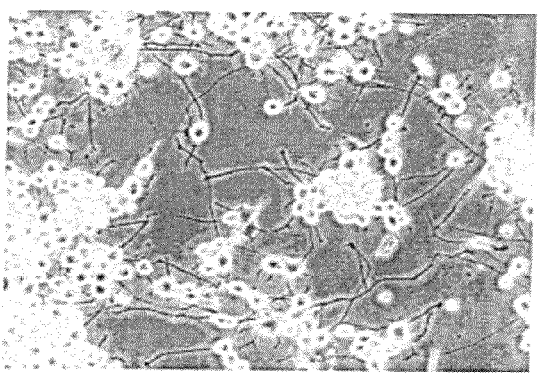
Figure 4:
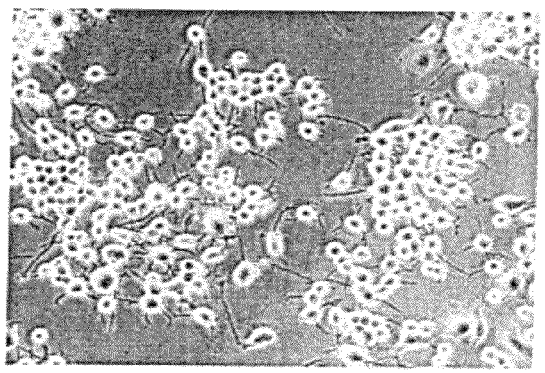
Figure 4:
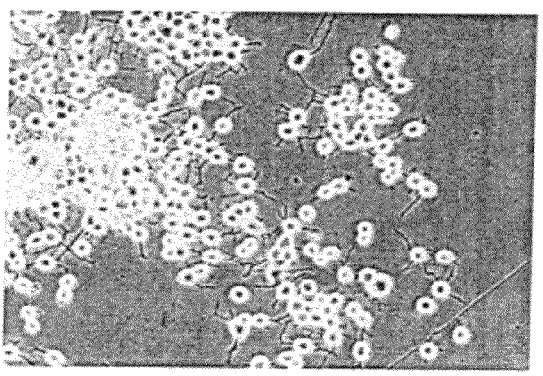
Figure 4:
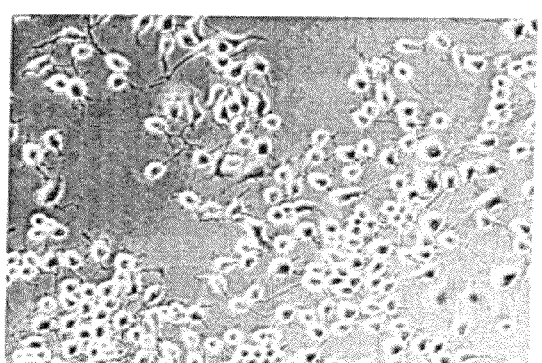

Then, two days after addition of the various test samples, neurite elongation activities were observed under microscope. FIG. 4 show picture images for comparing the neurite elongation activities exerted by the various test samples in cultures.

As shown in the images, the monodemethylated products, i.e., 4'-demethylnobiletin and 4'-demethyltangeretin were found to have significant neurite elongation activities compared with the comparative controls, i.e., nobiletin and tangeretin.

In addition, Gu H. et al. (Neurosci Lett. 2009, 453, 204) show that a dementia model administered with a neurotrophic factor having a neurite elongation activity has a memory-improving activity and an anti-Alzheimer's activity. Therefore, the results of this example strongly suggest that 4'-demethylnobiletin and 4'-demethyltangeretin have memory-improving activities and anti-Alzheimer's activities.

Example 7

Fermentation of Fruit Skin of *Citrus reticulata* (Another Name: Ponkan) by *Aspergillus* Mold (*Aspergillus kawachii*)

An *Aspergillus* mold-fermented product was obtained in the same manner as in Example 1 except that fermentation by the *Aspergillus* mold was performed using *Aspergillus kawachii* (manufactured by Bioc) as an *Aspergillus* mold (it should be noted that the fermentation period was 4 days).

Then, the resultant fermented product was subjected to an HPLC analysis, and the results showed that nobiletin and tangeretin present before the fermentation disappeared completely, and after fermentation, showed peaks of compounds modified into 4'-demethylnobiletin and 4'-demethyltangeretin.

Example 8

Fermentation of Fruit Skin of *Citrus reticulata* (Another Name: Ponkan) by *Aspergillus* Mold (*Aspergillus oryzae*)

An *Aspergillus* mold-fermented product was obtained in the same manner as in Example 1 except that fermentation by the *Aspergillus* mold was performed using *Aspergillus oryzae* (manufactured by Bioc) as an *Aspergillus* mold (fermentation period: 10 days).

Then, the resultant fermented product was subjected to an HPLC analysis, and the results showed that nobiletin and tangeretin present before the fermentation disappeared completely, and after fermentation, showed peaks of compounds modified into 4'-demethylnobiletin and 4'-demethyltangeretin.

Example 9

Study on Memory-Improving Activity (1) Preparation of Test Sample

First, a composition containing the demethyl polymethoxyflavonoids at high contents was prepared in the same manner as in Example 2.

2 g of the composition were dissolved in 20% methanol and subjected to ODS column chromatography (a column with an inner diameter of 20 mm and a length of 30 cm was filled with 30 g of Wakogel 50C18), and components eluted with 40% methanol were removed, followed by elution with 60% methanol, to thereby obtain 250 mg of a mixture of 4'-demethylnobiletin and 4'-demethyltangeretin. The mixture was used to study an effect on memory improvement.

(2) Animal Test

As an evaluation system for memory improvement, a spatial memory test for scopolamine-induced spatial memory impairment was performed using a Y-shaped maze apparatus. This test is a test frequently used for examining a spatial working memory ability based on a behavior characteristic (alternation behavior) by which an animal avoids an arm where the animal entered at the last minute and enters another arm.

In this test, an acrylic black trapezoidal arm (floor width: 3 cm, sidewall height: 12 cm, open ceiling width: 10 cm, length: 40 cm) was used as the mouse Y-shaped maze apparatus. Three arms in the apparatus were named A, B, and C, and first, a mouse was placed on the end of A and left to move freely in the Y-shaped maze for 8 minutes. The arms where the mouse entered were recorded in order. The number of times the mouse entered each arm ("total arm entries") and the number of the case where the mouse chose consecutively different three arms (number of the alternation behavior) were counted, and a value was calculated based on the equation: number of alternation behavior÷(total arm entries−2)×100=alternation behavior (%) and used as an index of spontaneous alternation behavior.

In this test, ddY mice (male, body weight 25 to 30 g, n=6) were used. First, at the start of the test, the Y-shaped maze test was performed, and the mice were divided into two groups (test sample administration group and control group) so that the alternation behaviors were almost even between the two groups.

Further, 4'-demethylnobiletin and 4'-demethyltangeretin (suspended in physiological saline containing 0.5% Tween 20) obtained as described above were orally administered repetitively to the mice in the test sample administration group at a rate of 30 mg/body weight kg/day. It should be noted that physiological saline containing 0.5% Tween 20 was orally administered repetitively to the mice in the control group.

Then, after one-week repetitive administration, scopolamine was administered subcutaneously to each mouse at a dose of 0.6 mg/kg (dissolved in physiological saline), and 30 minutes after administration, the Y-shaped maze test was performed again.

Figure 5:
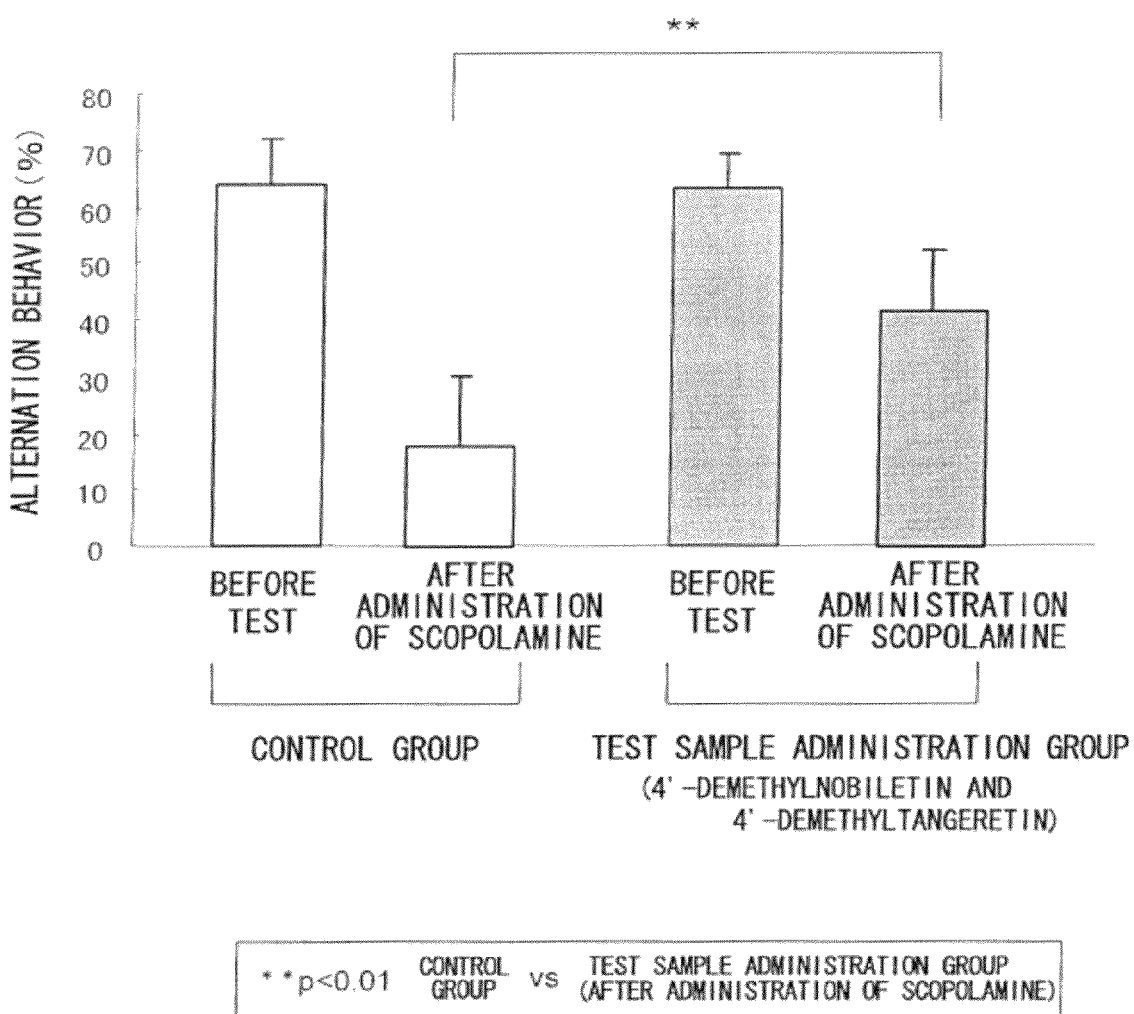
FIG. 5 is a graph for comparing spontaneous alternation behaviors (an index representing a spatial working memory) when test samples were administered to mice in Example 9.

FIG. 5 shows the results. (It should be noted that, in FIG. 5, the significant difference indicated by "**" represents a risk rate of 1% or less.)

As a result, in the case of the control group (administration of only physiological saline containing 0.5% Tween 20), the alternation behavior significantly decreased by administration of scopolamine compared with that before the start of the test.

On the other hand, in the case of the test sample administration group (administration of 4'-demethylnobiletin and 4'-demethyltangeretin), the alternation behavior was significantly high compared with that before the start of the test.

The results strongly suggest that 4'-demethylnobiletin and 4'-demethyltangeretin have scopolamine-induced spatial memory impairment-improving activities and have memory-improving activities and anti-Alzheimer's activities.

INDUSTRIAL APPLICABILITY

The present invention enables simple and large-scale production of 4'-demethylnobiletin and 4'-demethyltangeretin, which are extremely useful functional components, by a highly safe method using a highly safe raw material.

Therefore, the present invention is expected to be used in the food or beverage and pharmaceutical preparation fields. Further, a high level of demand is expected in modern society where the rate of persons suffering from dementia or memory impairment is increasing as the population ages and the cause of death due to cancer accounts for a great proportion.

The invention claimed is:

1. A method for improving memory comprising administering to a patient in need thereof a pharmaceutically effective amount of 4'-demethylnobiletin.

* * * * *